United States Patent [19]

Oppliger et al.

[11] Patent Number: 5,184,499

[45] Date of Patent: Feb. 9, 1993

[54] TESTING DEVICE WITH ACCELERATION TUBE

[75] Inventors: Erich Oppliger, Heimberg; Martin Monkewitz, Lucerne, both of Switzerland

[73] Assignee: Schweizerische Eidgenossenschaft vertreten durch die Eidg. Munitionsfabrik Thun der Gruppe fur Rustungsdienste, Thun, Switzerland

[21] Appl. No.: 647,269

[22] Filed: Jan. 29, 1991

[30] Foreign Application Priority Data

Jan. 31, 1990 [CH] Switzerland .................. 00309/90

[51] Int. Cl.$^5$ .................. G01N 3/30; F41A 21/46
[52] U.S. Cl. .................. 73/11.01
[58] Field of Search .................. 73/11, 12, 167; 42/75.02

[56] References Cited

U.S. PATENT DOCUMENTS

| | | | |
|---|---|---|---|
| 487,487 | 12/1892 | Mason | 42/75.02 |
| 3,019,073 | 1/1962 | Hall | 73/167 |
| 3,034,335 | 5/1962 | Muller et al. | 73/35 |
| 3,426,578 | 2/1969 | Bergs et al. | 73/12 |
| 3,597,969 | 8/1971 | DiCarchack | 73/12 |
| 3,792,354 | 2/1974 | Slaght et al. | 73/167 |
| 3,805,608 | 4/1974 | Schmidt et al. | 73/11 |
| 3,823,600 | 7/1974 | Wolff | 73/12 |
| 4,349,200 | 9/1982 | Wakefield | 73/12 |

OTHER PUBLICATIONS

Mashimo, Tsutomo and Sawaoka, Akira, "A Measurement System for Interior Projectile Motion . . . Gas Gun," Japanese Journal of Applied Physics, vol. 20, No. 5, May, 1981, pp. 963–970.

*Primary Examiner*—Hezron E. Williams
*Assistant Examiner*—George M. Dombroske
*Attorney, Agent, or Firm*—Wegner, Cantor, Mueller & Player

[57] ABSTRACT

A testing device, especially for ignition elements, has an acceleration tube (3) with an acceleration piston (4) slidable therein. The space in the acceleration tube (3) between the piston (4) and an exit aperture (7) is connectable with a vacuum pump (10) to accelerate the acceleration piston (4). As soon as a retaining device (5) releases the acceleration piston (4), the latter is accelerated by atmospheric pressure in a direction towards the exit aperture (7). An impact body (6), releasably held in the acceleration piston (4), is adapted to release itself from the acceleration piston (4) as soon as the latter hits the end of the acceleration tube (3), and then flies out of the exit aperture (7) of the acceleration tube (3) against the test object. The invention can also be applied in the field of material testing and quality control.

9 Claims, 2 Drawing Sheets

TESTING DEVICE WITH ACCELERATION TUBE

The invention relates to a testing device with an impact body pneumatically acceleratable in an acceleration tube and adapted to be moved out of an exit aperture of the acceleration tube, for use especially for the testing of ignition elements.

When testing ignition elements, it is necessary for an impact body to impact the firing pin of the ignition element at a velocity settable with the highest possible accuracy. For different ignition elements, the impact velocity of the impact body must be variable over a wide range, while still being settable with the highest possible accuracy, in order to obtain reproducible test results. For other test purposes, too, it is frequently important for the impact body to impact the test object at a precisely presettable velocity.

As shown by the U.S. Pat. No. 4,349,200, a testing device is already known in which an impact body is accelerated in an acceleration tube by overpressure in a pressure storage vessel, with highly pressurized helium being provided as the pressure medium. During the movement of the impact body in the acceleration tube, as gas from the storage vessel flows into the acceleration tube, the pressure in the pressure storage vessel drops, whereby the pressure force driving the impact body continuously decreases during the acceleration process. Even with identical initial pressures, this continuously decreasing pressure produces differences in the velocity of the impact body upon exiting the acceleration tube.

It is an object of the invention to design a testing device of the above-mentioned type in such a way as to facilitate extensive variation of the exit velocity of the impact body, while maintaining a maximum accuracy for each setting.

According to the invention, this object is achieved by providing a shutter at the exit aperture which opens upon impact of the impact body so that, in its initial position, the impact body is sealingly retained at the side of the acceleration tube which is located opposite to the exit aperture, and so that the space in the acceleration tube between the impact body and the exit aperture is effectively connected with a source of negative pressure.

In such a testing device, the impact body is driven by atmospheric pressure. The force driving it hardly changes, provided that the cross-sections of the atmospheric-air access openings are approximately equal to the inner cross-section of the acceleration tube.

Functionally, the testing device according to the invention is a linear accelerator. Due to this fact, it is possible to achieve very accurately reproducible impact velocities. It is furthermore possible to vary the impact velocities over a very wide range, without negatively affecting the reproducibility of the impact velocity of the impact body as set. The testing device according to the invention is particularly suitable for the testing of ignition elements, since their firing behavior is affected by the impact and penetration velocity of the firing pin. This factor can be optimally taken into consideration in the present invention because the velocity of the impact body reaching the firing pin of the ignition element is optimally settable.

It is possible to accelerate the impact body to particularly high terminal velocities without the need for an undesirably long acceleration tube if, according to a particularly advantageous feature of the invention, the impact body is releasably held in an acceleration piston sealingly guided in the acceleration tube and movable in the direction of the exit aperture against an abutment surface of the acceleration tube. The large surface area of the acceleration piston is thus available to be acted on by atmospheric pressure, while the impact body itself may have the usually desired small cross-section.

The impact body is easily inserted into the acceleration piston and is held in a sealing position by the negative pressure in the acceleration tube if, according to another feature of the invention, the acceleration piston is provided with a bore extending therethrough for accommodating the impact body, and if a shearable flange of the impact body can be made to abut a contact surface of the acceleration piston, which surface is located at the side of the bore that is facing away from the exit aperture. Upon impact of the acceleration piston on its abutment surface, this flange is cut-off the impact body by shearing action, so that the impact body is released from the acceleration piston and passes the shutter at the velocity of the acceleration piston. This embodiment also facilitates the use of different masses in order to control the depth of penetration of the firing pin into the ignition body. Alternatively, it is possible to provide a disengageable retaining mechanism instead of a shearable flange.

Another advantageous feature of the invention is that, at that end of the acceleration tube that is opposite to the exit aperture, there is provided a remotely controllable retaining mechanism for retaining and releasing the acceleration piston. This facilitates the retaining and releasing of the acceleration piston at a particularly low expenditure and in a simple manner. Release is preferably effected electrically or pneumatically, but can also be achieved by purely mechanical means.

The terminal velocity of the impact body is set very simply and with a high degree of reproducibility if, according to yet another feature of the invention, the retaining device is arranged to be slidable in the longitudinal direction of the acceleration tube.

The use of exchangeable acceleration tubes of different lengths is another way of predetermining the desired terminal velocity in a simple manner and over a widely varying range. Fixedly mounting the acceleration tubes is advantageously effected by supports or slides of the kind known from lathes.

For the precise setting of the impact velocity, it is advantageous if the acceleration tube is provided with a velocity measuring device for determining piston velocity immediately prior to hitting the abutment surface at the exit-aperture side.

The velocity of the exiting impact body can be exactly determined if a second velocity measuring device is provided behind the exit aperture of the acceleration tube for determining the velocity of the exiting impact body.

The testing device is particularly well designed for the testing of ignition elements if, according to another feature of the invention, the acceleration tube and a test-object mount are arranged in mutual alignment and adapted to be slidable along longitudinal guideways.

The retention of the acceleration body in the acceleration tube can be easily effected if the acceleration piston is provided on the exit-aperture-facing side of the acceleration body with an inwardly pointing flange for the engagement, therebehind, of retaining projections of the retaining device.

An embodiment of particularly simple design of the retaining device includes two scissor-type levers connected by a joint, with a retaining projection provided on each of the piston-facing ends, and with slanting surfaces which diverge from the joint being provided on the oppositely pointing ends. An actuating piston, adapted to move in between the slanting surfaces by means of a pneumatic cylinder is provided to cause the retaining projections to swing inwardly.

The shutter of the exit aperture can be of several designs. It could, for instance, be a valve flap, opening upon impact of the impact body. Of particular simple design, however, is the shutter formed by a membrane destroyable by the impact body, for instance, by a foil adhesively attached at its edges.

The invention admits of many embodiments. For the further clarification of its basic principles, one of them has been represented in the drawings and is described in the following.

Figure 1:
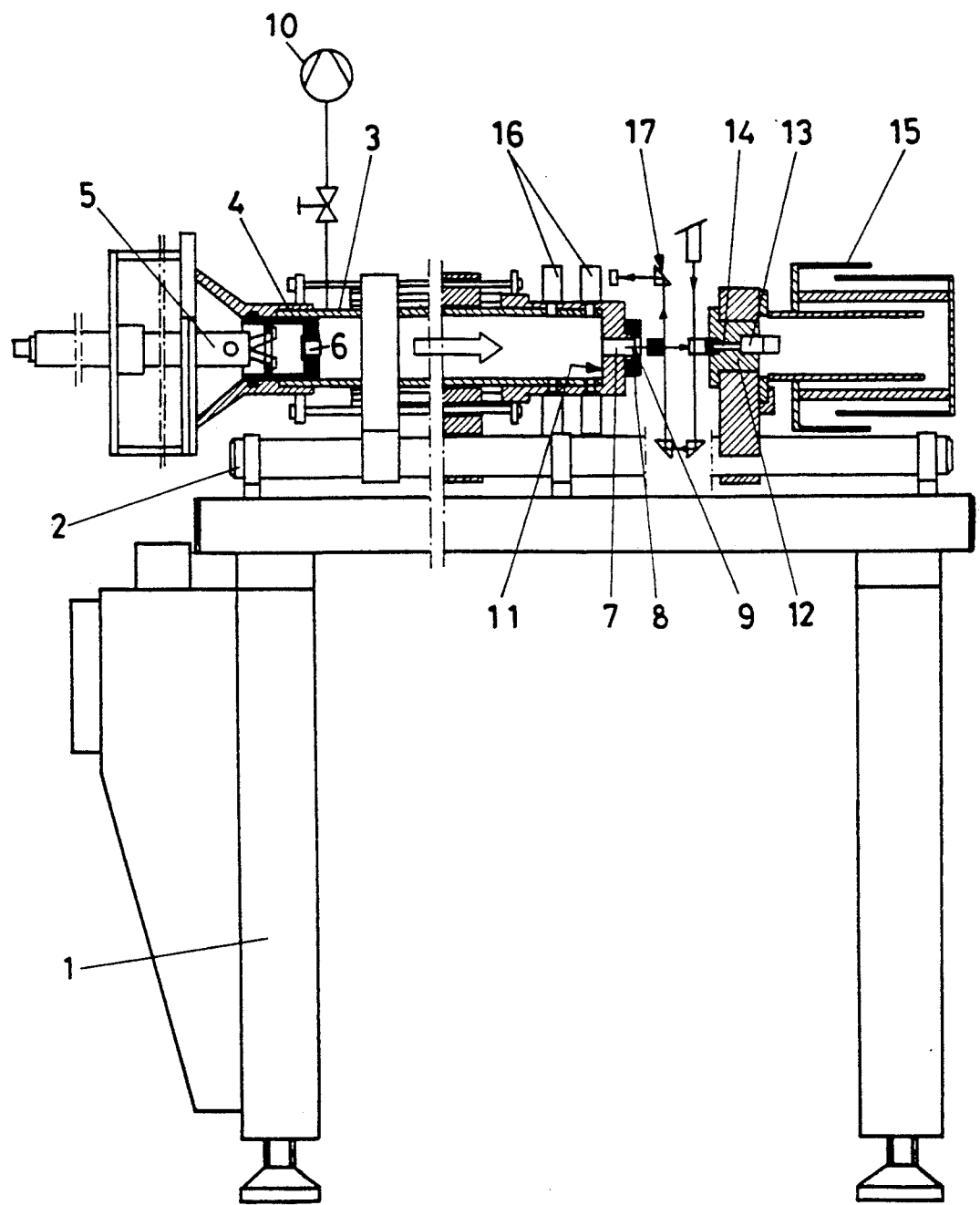
FIG. 1 is an elevational view, shortened and in partial cross-section, of the testing device.

FIG. 1 shows a stand 1 provided with longitudinal guideways 2, on which an acceleration tube 3 is slidably mounted so as to be arrestable at any position. As seen in FIG. 1, an acceleration piston 4 is provided on the left side of the aooeleration tube and adapted to slide therein, the piston being retained in the basic position shown by a retaining device 5. The acceleration piston 4 carries an impact body 6 in its frontal surface facing away from the retaining device 5.

The acceleration tube 3 has an exit aperture 7 at the end opposite to the retaining device 5, which the impact body 6 freely fits, and which is airtightly closed by a shutter 8. This shutter 8 is provided with a thin membrane 9 which is destroyed upon impact of the impact body 6, so that the impact body can pass through the exit aperture 7.

An important component of the object of the invention is a vacuum pump 10 which facilitates the evacuation of the space in the acceleration tube 3 between the exit-aperture-facing frontal surface of the acceleration piston 4 and the exit aperture 7. The frontal surface of the acceleration piston 4 facing away from the exit aperture 7 is exposed to atmospheric pressure. When the retaining device 5 releases the acceleration piston 4, the latter slides with increasing velocity towards the exit aperture 7, until it hits an abutment surface 11 at the exit-aperture side. At this point, the impact body 6 can free itself from the acceleration piston 4, and flies out of the acceleration tube 3.

A test-object mount 12 is arranged on the longitudinal guideways 2 in alignment with the acceleration tube 3, equally slidable on the guideways 2 and fixable in any desired position. The test-object mount accommodates a test object 13 which, in the case of this embodiment, is an ignition element with a firing pin 14. As the firing pin 14 has a substantially lower mass than the impact body 6, it moves into the ignition element, after being impacted by the impact body 6, at a velocity considerably higher than the impact velocity of the impact body 6. During use of the testing device, a fragment protector 15 provides protection from fragments of the ignition element and from resulting pressure waves.

To determine the velocity of the acceleration piston 3 immediately prior to its hitting the abutment surface 11, a velocity measurement device 16 is provided at the acceleration tube 3. A second velocity measurement device 17 is located between the exit aperture 7 of the acceleration tube 3 and the test-object mount 12. The second velocity measurement device 17 serves for the precise determination of the velocity of the impact body 6 after its exit from the acceleration tube 3 and operates in a known manner with laser light.

Figure 2:
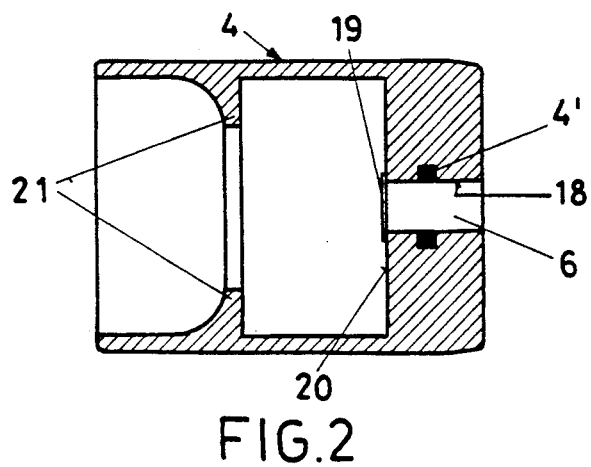
FIG. 2 is a cross-sectional view, to a larger scale relative to FIG. 1, of an acceleration piston of the testing device, including an inserted impact body.

FIG. 2 clearly shows the design of the acceleration piston 4. As can be seen in FIG. 2, the impact body 6 is inserted from the left side into a coaxial bore 18 of the acceleration piston. The impact body 6 has a flange 19 which abuts against a contact surface 20 of the acceleration piston 4 that faces the retaining device 5. The flange is dimensioned so that, upon the acceleration piston 4 hitting the contact surface 20 shown in FIG. 2, the flange shears off, thereby releasing the impact body 6. An O-ring, seated in an annular groove 4' serves as a sealing element.

It is further seen in FIG. 2 that the acceleration piston 4 is provided with an inwardly directed flange 21 on its side facing the retaining device 5, behind which the retaining device 5 can engage, so as to retain the acceleration piston 4 in the basic position shown in FIG. 1.

Figures 3, 4:
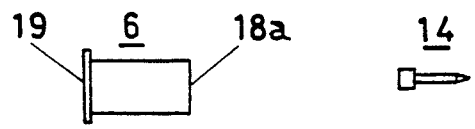
FIG. 3 shows the impact body of FIG. 2.
FIG. 4 shows the firing pin to true scale, prior to its insertion into the test body mount.

FIG. 3 shows the impact body 6 with its flange 19 and its impact surface 18a in front of the firing pin 14 shown in FIG. 4 prior to the insertion of the latter into the test-object mount 12, as shown in FIG. 1.

Figure 5:
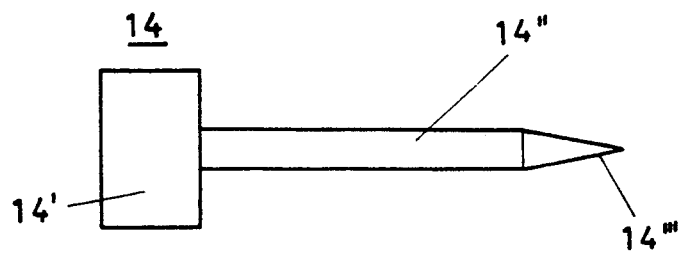
FIG. 5 represents the firing pin of FIG. 4 to a larger scale.

FIG. 5 shows the design of the firing pin 14 to better advantage, indicating its flange 14', its cylindrical portion 14" and its point 14'".

Figure 6:
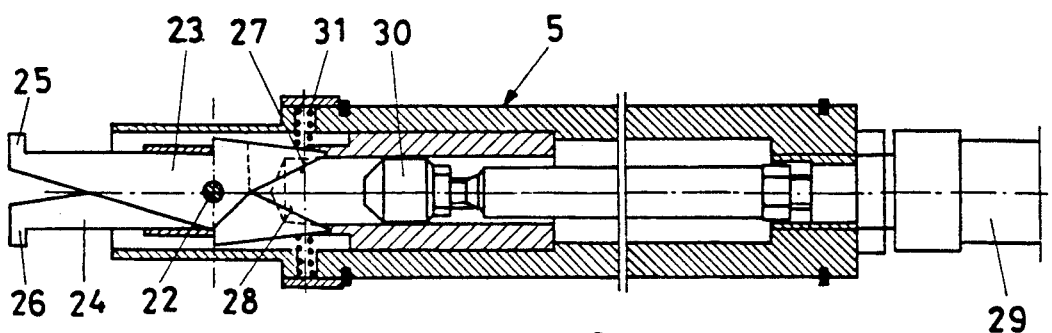
FIG. 6 is a view, in longitudinal cross-section, of a retaining device of the testing device.

FIG. 6 illustrates the design of the retaining device 5. The latter is seen to comprise two scissor-type levers 23, 24, each of the free ends of which is provided with an outwardly pointed retaining projection 25, 26, which are able to engage the latter from behind its flange 21 for retaining the acceleration piston 4. The scissor-type levers 23, 24 are provided with slanting surfaces 27, 28 on the opposite side of the levers, which diverge from the side of the joint 22. A pneumatic cylinder 29 is able to move an actuating piston 30 against the slanting surfaces 27, 28, causing the scissor-type levers to be swiveled in such a way that the retaining projections 25, 26 are swung radially inside, thereby releasing the acceleration piston 4. Springs 31 maintain the slanting surfaces in the position shown.

Although the invention has been described as being provided for the development and testing of mechanical ignition elements, it is suited for universal usage, such as in the calibration of acceleration sensors, of safety elements, as well as the testing of electronic and mechanical building elements under precise mechanical load conditions. Also envisaged is the use in the field of quality control.

We claim:

1. A testing device with an impact body pneumatically acceleratable in an acceleration tube and adapted to be moved out of an exit aperture of the acceleration tube comprising:

a shutter provided at the exit aperture of the acceleration tube which opens upon the impact of the impact body wherein, in the initial position, the impact body is sealingly retained at the side of the acceleration tube which is located opposite to the exit aperture, and wherein the space in the acceleration tube between the impact body and the exit aperture is operatively connected with a source of negative pressure;

wherein the impact body is releasably held within a bore extending through an acceleration piston, said acceleration piston being slidable within the acceleration tube in the direction of the exit aperture against an abutment surface of the acceleration tube; and wherein the impact body has a shearable flange which can be made to abut a contact surface of the acceleration piston, said contact surface being located at that side of the bore that is facing away from the exit aperture.

2. A testing device with an impact body pneumatically acceleratable in an acceleration tube and adapted to be moved out of an exit aperture of the acceleration tube comprising:

a shutter provided at the exit aperture of the acceleration tube which opens upon the impact of the impact body wherein, in the initial position, the impact body is sealingly retained at the side of the acceleration tube which is located opposite to the exit aperture, and wherein the space in the acceleration tube between the impact body and the exit aperture is operatively connected with a source of negative pressure; and a remote-control retaining device is provided at the end of the acceleration tube which is opposite to the exit aperture for retaining and releasing of the acceleration piston, wherein the retaining device is arranged to be slidable in the longitudinal direction of the acceleration tube.

3. The testing device according to claim 1, wherein the acceleration tube is exchangeable.

4. The testing device according to claim 1, wherein the acceleration tube is provided with velocity measuring means for determining piston velocity immediately prior to hitting the abutment surface at the exit-aperture side.

5. The testing device according to claim 4, further comprising second velocity measuring means for determining the velocity of the exiting impact body, said second velocity measuring means being disposed beyond the acceleration tube and behind its exit aperture.

6. The testing device according to claim 1, wherein the acceleration tube and a test object mount are arranged in mutual alignment and adapted to be slidable along longitudinal guideways.

7. The testing device according to claim 2, wherein the acceleration piston is provided with an inwardly pointing flange on its side facing away from its exit aperture for engaging, therebehind, retaining projections of the retaining device.

8. The testing device according to claim 7, wherein the retaining device includes two scissor-type levers connected by a joint, each of the lever ends that face the accelerating piston having one of the retaining projections, and each of the oppositely pointing ends of which have slanting surfaces which diverge from the joint, and wherein an actuating piston is provided which moves in between the slanting surfaces by means of a pneumatic cylinder to cause the retaining projections to swing inwardly.

9. The testing device according to claim 1 wherein the shutter includes a membrane destroyable by the impact body.

* * * * *